United States Patent [19]  [11] 4,329,590
Adelmeyer  [45] May 11, 1982

[54] X-RAY EXAMINATION APPARATUS

[75] Inventor: Dieter Adelmeyer, Erlangen, Fed. Rep. of Germany

[73] Assignee: Siemens Aktiengesellschaft, Berlin & Munich, Fed. Rep. of Germany

[21] Appl. No.: 184,526

[22] Filed: Sep. 5, 1980

[30] Foreign Application Priority Data

Sep. 28, 1979 [DE] Fed. Rep. of Germany ....... 2939425

[51] Int. Cl.$^3$ ................................................. A61B 6/00
[52] U.S. Cl. ................................ 250/511; 250/416 R
[58] Field of Search ............ 250/511, 513, 449, 416 R

[56] References Cited

U.S. PATENT DOCUMENTS 2,921,202  1/1960  Berger et al.
3,947,689  3/1976  Wagner ............................... 250/511
4,099,063  7/1978  Pury et al. ........................... 250/513

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a roentgenographic installation, an x-ray tube aligned with respect to the roentgenographic installation, a flange-mounted, motor adjustable primary radiation diaphragm, and a patient support which is respectively longitudinally displaceable between the x-ray tube and the roentgenographic installation. The x-ray examination apparatus possesses a program control installation, with which the patient support can be displaced in a step-by-step fashion relative to the roentgenographic installation in predetermined time intervals. During angiography of the extremities, the photographic exposure field changes in size as a consequence of the advancement of the contrast medium and the related displacement of the patient support plate relative to the photographic exposure installation. This can result in lateral halations of the examination area. In order to prevent this, the disclosure provides that a diaphragm control circuit is connected to the program control installation which allocates to every photographic exposure position, actuatable by the program control installation, a separately preselectable setpoint value for the diaphragm follow-up control.

5 Claims, 3 Drawing Figures

X-RAY EXAMINATION APPARATUS

BACKGROUND OF THE INVENTION

The invention relates to an x-ray examination apparatus comprising a roentgenographic installation, an x-ray tube oriented toward the roentgenographic installation, a collimator or primary radiation diaphragm which is flange-mounted to the x-ray tube and adjustable by a motor via a follow-up motor controller, and a program control installation for effecting the automatic step-by-step shifting of the patient support relative to the roentgenographic installation and relative to the x-ray tube which is aligned with respect to the roentgenographic installation.

X-ray examination apparatus, which possess a program control installation for the automatic step-by-step displacement of the patient support relative to the roentgenographic installation and relative to the x-ray tube which is aligned to the roentgenographic installation, are preferably employed in the case of angiography of the extremities. In this examination apparatus, a contrast medium is injected into the vascular system to be examined; for example, into the leg artery, and the diffusion of the contrast medium is followed roentgenographically. For this purpose, photographs are prepared at brief, preselectable time intervals which permit statements regarding the nature and the chronological progression of the diffusion of the contrast medium in the vascular system. On account of the diffusion speed of the contrast medium, which is, in part, quite high in the larger vessels, sometimes not only are rapid photographic series with up to four images per second necessary, but also the photographic exposure field must be displaced, at predetermined time intervals of up to approximately two seconds between every two photographs, respectively, by the amount of the distance traveled in the meantime by the contrast medium.

Because of such rapid movement the procedure can no longer be precisely carried out manually; and, in the case of known x-ray examination apparatus, program control installations are employed which bring about the adjustment of the motor-displaceable patient support by a preadjustable distance between the individual photographic exposures. However, instead of this, the x-ray tube and the roentgenographic installation have also already been displaced while the patient support remains stationary.

It is a peculiar feature of this examination technique that, in particular in the case of examination of the extremities, the image quality becomes somewhat poorer from photographic exposure to photographic exposure. On account of the increasing tapering or reduction in size of the extremities, gradually a lateral halation of the examination area occurs. The x-radiation passing laterally by the extremity impinges on the image layer or film in a nonattenuated fashion. In the case of x-ray examination apparatus with automatic exposure timers, this leads to erroneous exposures of the examination area.

SUMMARY OF THE INVENTION

The object underlying the invention resides in pointing out a way, in the case of x-ray angiography of the extremities, as to how the image quality can be improved during the photographic exposure series and the radiation exposure of the patient can be reduced.

Therefore, in the case of an x-ray examination apparatus of the type initially cited, in accordance with the invention, there is connected to the program control installation, a diaphragm control circuit which allocates, to every photographic exposure position which can be activated by the program control installation, a separately preselectable nominal or setpoint value for the diaphragm follow-up control. Through this construction it becomes possible to select, yet prior to the injection of the contrast medium, the optimum diaphragm adjustment for every individual photographic exposure field, and to set said diaphragm adjustment on the diaphragm control circuit. With every new adjustment of the photographic exposure field, effected by the program control installation, not only is the patient then displaced relative to the x-ray installation but also the collimator or primary radiation diaphragm of the x-ray tube is adjusted to the preselected desired value for the new photographic exposure field. This has as a consequence that lateral halations of the examination area, which impair the image quality, can be entirely avoided. Qualitatively improved photographic exposure series can thereby be provided in the case of angiography of the extremities. Simultaneously also every superfluous radiation exposure of the patient can thus be avoided because every photographic exposure field can be independently adjusted to be as great as is actually necessary for the diagnosis position.

Further details of the invention shall be explained in greater detail on the basis of two exemplary embodiments illustrated in the Figures on the accompanying drawing sheets; and other objects, features and advantages will be apparent from this detailed disclosure and from the appended claims.

DETAILED DESCRIPTION

Figure 1:
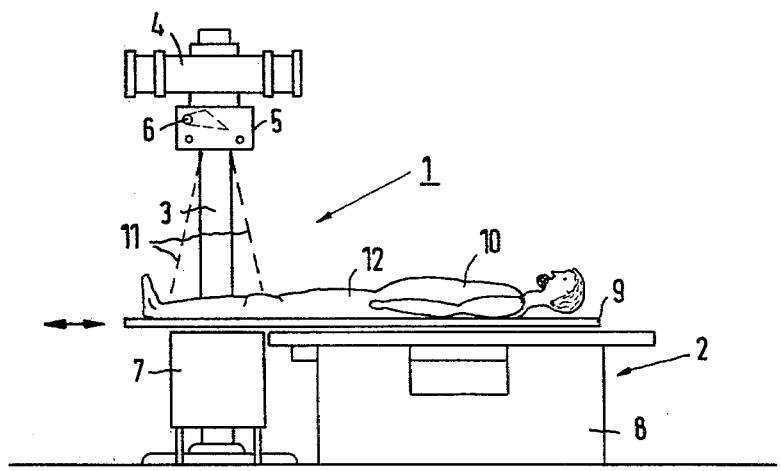
FIG. 1 illustrates a view of an x-ray examination apparatus suitable for angiographs of the extremities.

In FIG. 1 an x-ray examination apparatus 1 is apparent comprising an x-ray examination table 2 and an x-ray support column 3, which is displaceable in the table-longitudinal direction, and is located behind the examination table 2 in the illustration of FIG. 1, with an x-ray tube 4 support-mounted above the x-ray examination table. A collimator or primary radiation diaphragm 5 with a full-field light-beam localizer 6 is flange-mounted to the x-ray tube. A roentgenographic installation 7, in the present instance, a sheet film changer, is installed next to the x-ray examination table 2. On the table support stand 8 of the x-ray examination table 2 a patient support plate 9—displaceable in the table longitudinal direction—with a patient 10 lying on top can be recognized. The sheet film changer 7 extends so far upwards that the patient support plate 9 just barely has clearance for horizontal movement above the changer 7. The cone of x-rays 11 aligned onto the sheet film changer 7 is indicated by broken lines.

Figure 2:
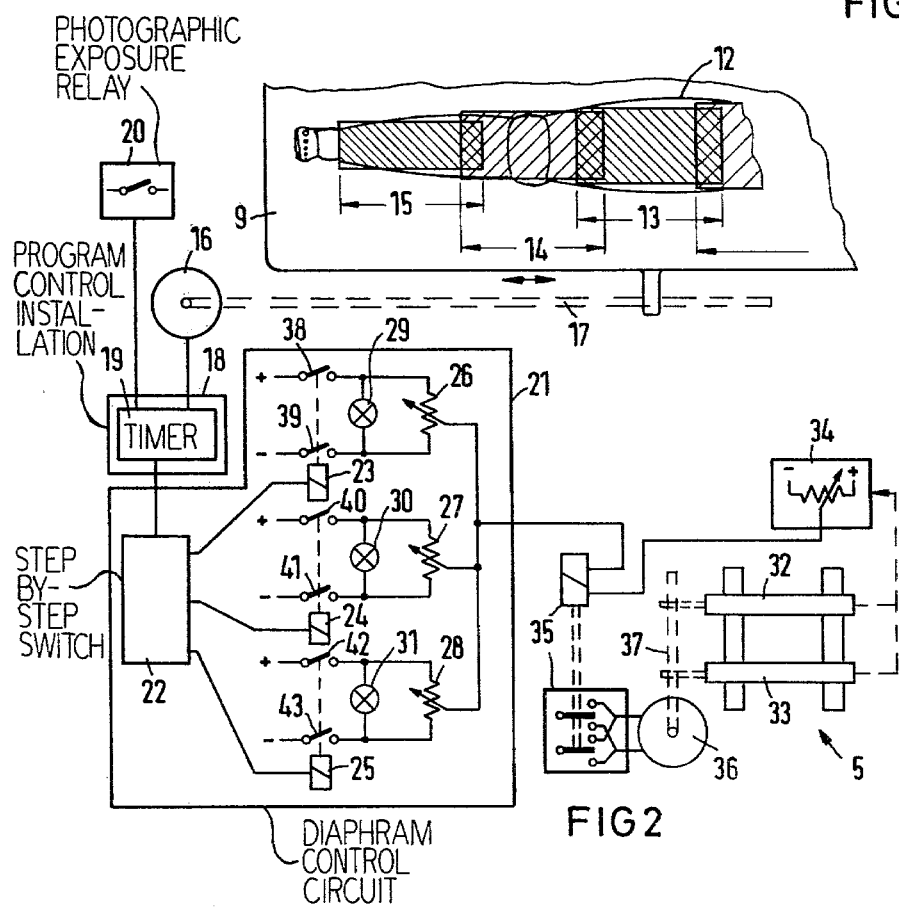
FIG. 2 shows a schematic illustration of the circuit arrangement for the automatic analog adaptation or matching of the diaphragm adjustment to the individual photographic exposure fields.

FIG. 2 shows, in schematic illustration, a portion of the patient support plate 9 in plan view as well as the leg 12 of the patient 10 which is lying on the patient support plate. Over the leg, the mutually overlapping photographic exposure fields 13, 14, 15, desired by the physician, are illustrated in a hatched fashion. They differ in their width transversely to the longitudinal direction of the table. Next to the patient support plate 9, a spindle 17 is indicated, driven by a servomotor 16, for the displacement of the patient support plate 9 in the table-longitudinal direction. The servomotor 16 is connected to a program control installation 18. The program control installation, which comprises a time switch or timer 19, controls, with the time switch, the servomotor 16 for the displacement of the patient support plate 9 and a so-called photographic exposure relay 20 for triggering the individual x-ray photographs. There is moreover connected to the time switch 19 a diaphragm control circuit 21. The diaphragm control circuit 21 contains a stepping mechanism or step-by-step switch 22 and as many relays 23, 24, 25, which can be individually activated by the stepping mechanism 22, as there are photographic exposure fields 13, 14, 15 which can be maximally activated with the program control installation 18. By means of each of these relays, a so-called nominal or setpoint value potentiometer 26, 27, 28 can be connected to a voltage source. Connected in parallel with every nominal value potentiometer is a signal lamp 29, 30, 31. The nominal value potentiometers 26, 27, 28 form one branch of a resistance bridge in whose other branch an actual value potentiometer 34, coupled with the diaphragm plates 32, 33 is connected. In the diagonal of the bridge circuit a bipolar switching relay 35 is connected via which the diaphragm plate adjustment motor 36 can be switched on in the one or the other rotational direction depending upon the polarity sign of the voltage in the bridge diagonal. The diaphragm plate adjustment motor 36 drives a spindle 37 via which the diaphragm plates 32, 33 are adjustable, the plates 32, 33 being aligned parallel to the longitudinal axis of the patient support plate 9. The actual value potentiometer 34 is adjusted according to the movement of said diaphragm plates.

Through the time switch or timer 19 of the program control installation 18 the photographic exposure relay 20, with which the x-ray tube 4 is switched on, is triggered in the time intervals specified or predetermined by the physician. Moreover, the servomotor 16 for the displacement of the patient support plate 9 via the program control installation 18 is switched on in the time intervals between two photographic exposures, respectively. Through the servomotor 16, the patient support plate 9, in a manner not further illustrated herein, is then displaced by distances which are preadjustable on the x-ray examination apparatus 1. This has as a consequence the fact that, in the photographic exposure intervals preadjusted by the physician, x-ray photographic exposures of the respective extremity 12 of the patient 10 are prepared which are mutually shifted by the specified or predetermined distance by which the contrast medium is carried along through the bloodstream in the time interval between the photographic exposures.

Simultaneously with the switching-on of the servomotor 16 for the displacement of the patient support plate 9 into a new photographic exposure position, the stepping mechanism 22 of the diaphragm control circuit 21 of the program control installation 18 is further advanced and, by means of the stepping mechanism, changeover switching is effected to another relay of the relays 23, 24, 25. Each one of the relays 23, 24, 25 of the diaphragm control circuit 21 which is switched on connects, with its contact sets 38 to 43, a nominal value potentiometer 26, 27, 28 to voltage. The nominal value potentiometer—switched on by a relay, respectively—at which the diaphragm nominal value can be adjusted by the physician, forms the one branch of a resistance bridge. The other branch of the resistance bridge is formed by the actual value potentiometer 34 which is controlled by means of the diaphragm plates 32, 33. In the case of lacking correspondency of the actual value and nominal value resistances, the bipolar switching relay 35, connected in the bridge diagonal, is connected to voltage. It switches on the diaphragm plate adjustment motor 36 with corresponding rotational direction, depending upon the polarity of the voltage in the bridge diagonal, for so long until the diaphragm plates 32, 33 and the actual value potentiometer 34, coupled with the diaphragm plates, are adjusted to such an extent that the resistance bridge is again balanced.

Thus, with the nominal value potentiometers 26, 27, 28 of the diaphragm control circuit 21, the position of the diaphragm plates 32, 33, desired by the physician, can be separately preadjusted for every photographic exposure position. During angiography, the diaphragm plates 32, 33 of the collimator or primary radiation diaphragm 5 are then automatically driven into this preadjusted photographic exposure position by the diaphragm plate adjustment motor 36, as soon as the stepping mechanism 22, activated by the time switch 19 of the program control installation 18, has, simultaneously with the servomotor 16, switched on the corresponding nominal value potentiometer via its relay.

The consequence of this is that the individual series photographic exposures, during angiography of the extremities, are mutually displaced, not only by the predeterminable distance traveled by the contrast medium in the time interval between the individual x-ray photographic exposures, but that simultaneously also a diaphragm aperture or opening, which is separately preadjustable on the nominal value potentiometers of the diaphragm control circuit 21 for every individual photographic exposure field 13, 14, 15, is adjusted by the diaphragm plate adjustment motor 36 as soon as the respective photographic exposure field is attained. Not only is the quality of the photographic exposures improved thereby, but also the radiation exposure of the patient is reduced.

Figure 3:
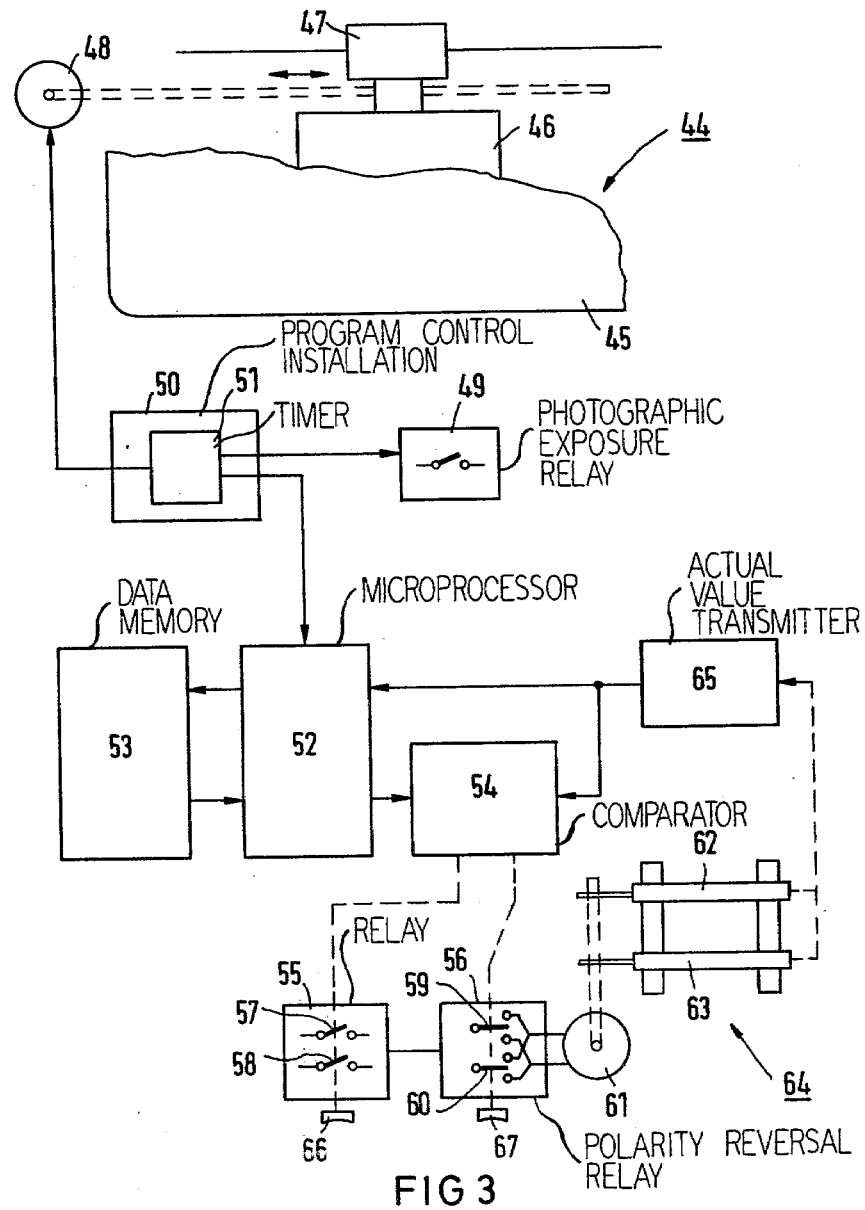
FIG. 3 shows a schematic illustration of another x-ray examination apparatus in which the adaptation or matching of the diaphragm adjustment to the individual photographic exposure fields proceeds in digital technology.

FIG. 3 shows, in a schematic illustration, another x-ray examination apparatus 44 which is likewise suitable for the preparation of angiographs and in which, not the patient support plate 45, but a roentgenographic installation 46, disposed beneath the patient support plate, together with a tube support column 47 coupled thereto, are displaceable in the longitudinal direction of the patient support plate 45 by a servomotor 48. In this instance, also, the servomotor 48 and a photographic exposure relay 49 are connected to a program control installation 50. Both are controlled by a preadjustable time switch or timer 51 installed in the program control installation. The same applies to a microprocessor 52 connected to the program control installation. The latter microprocessor 52 is connected with a data memory 53, on the one hand, and with a comparator 54, on the other hand. A relay 55 and a polarity reversal relay 56 are controlled by the comparator 54. Their two contact sets 57 through 60 are connected in series with a diaphragm plate adjustment motor 61. By means of the diaphragm plate adjustment motor 61, similar to the exemplary embodiment of FIG. 2, the diaphragm plates 62, 63 of the collimator or primary radiation diaphragm 64, which are aligned parallel to the displacement direction of the roentgenographic installation 46, as well as an actual value transmitter 65, coupled with the diaphragm plates, are adjusted. The actual value transmitter 65, whose output signals are present in digital form, is connected to the microprocessor 52 as well as to the comparator 54.

If an angiograph is to be made with this x-ray examination apparatus 44, the physician first determines, on the basis of the extremity to be examined, the time intervals between the individual photographic exposures, and adjusts the latter on the time switch 51 of the program control installation 50. The physician then will adjust, in a manner not further illustrated here, on the x-ray examination apparatus 44, a setting according to the distance traveled by the contrast medium in the adjusted time interval, for determining advance or forward feed distance for the roentgenographic installation 46 coupled with the tube support column 47. Subsequently, he can have every individual photographic exposure position be separately activated via the program control installation 50 prior to actual operation of the x-ray tube, and, in this photographic exposure position, he can adjust, at will, the diaphragm plates 62, 63 with the assistance of the light beam localizer of the collimator or primary radiation diaphragm 64, with the keys 66, 67. Upon adjustment of the diaphragm plates 62, 63, the actual value transmitter 65, coupled with the diaphragm plates 62, 63 is jointly adjusted. Its output signal is connected to the microprocessor 52, which is through-connected, by means of the program control installation 50, to the memory position of the data memory 53, which position is associated with the activated photographic exposure field. As a consequence of this, for every photographic exposure field, the respectively last adjustment of the diaphragm plates 62, 63 remains stored in the corresponding memory position of the data memory 53.

If, during the later angiography, the respective photographic exposure field is activated by the program control installation 50, the microprocessor 52 is also through-connected to the respectively associated memory location of the data memory 53. As a consequence, the data stored in this memory location are then connected to the comparator 54 as the nominal or setpoint value. The active setpoint value is compared with the data respectively simultaneously connected from the actual value transmitter 65 to the comparator 54, and the comparison leads to a corresponding control of the relay 55 and of the polarity reversal relay 56. By means of the relay 56, the diaphragm plate adjustment motor 61 is switched on in the desired rotational direction for such time duration until the actual value from transmitter 65 corresponds or agrees with the nominal value connected to the comparator 54, tapped from the data memory 53. Thus, also in the case of this x-ray examination apparatus 44, during angiography, in the case of every activated photographic exposure field, also the diaphragm plate adjustment, previously preselected by the physician for this photographic exposure field, is adjusted by the diaphragm plate adjustment motor 61.

It will be apparent that many modifications and variations may be effected without departing from the scope of the novel concepts and teachings of the present invention.

I claim as my invention:

1. X-ray examination apparatus comprising a patient support, a roentgenographic installation, an x-ray tube which is aligned with respect to the roentgenographic installation, a radiation diaphragm operatively associated with the x-ray tube and having an adjustment motor and a follow-up control for controlling said motor, and a program control installation for effecting the automatic step-by-step displacement of the patient support relative to the roentgenographic installation and relative to the x-ray tube which is aligned with respect to the roentgenographic installation, and a diaphragm control circuit (21, 52 through 56, 61, 65) connected to the program control installation (18, 50), and operable to allocate to each photographic exposure position which is capable of being activated by the program control installation, a separately preselectable setpoint value for the follow-up control so that the setting of the radiation diaphragm for each photographic exposure position can be preselected.

2. X-ray examination apparatus according to claim 1, characterized in that the diaphragm control circuit (21) comprises changeover switching for activating the setpoint value for each successive photographic exposure field (13, 14, 15), which changeover switching is controlled by the program control installation (18), and further comprises adjustable potentiometers (26, 27, 28) for successive connection by said changeover switching as the setpoint value transmitter into the circuit of the diaphragm follow-up control (26, 27, 28, 34 through 37).

3. X-ray examination apparatus according to claim 1, characterized in that the diaphragm control circuit (52 through 56, 61, 65) comprises a microprocessor (52), a data memory (53) for receiving preselected diaphragm setpoint values and a digital actual value transmitter (65), and a comparator (54) controls the diaphragm adjustment motor (61), in dependence upon the data connected from the actual value transmitter (65) and the data connected from the data memory via the microprocessor.

4. X-ray examination apparatus according to claim 3, characterized in that the comparator (54), in the case of noncorresponding data, activates a relay 55, lying with its contact sets (57, 58) in the current circuit of the diaphragm adjustment motor (61), and, in dependence upon the polarity of the data difference, activates a polarity reversal relay (56) with its contact sets (59, 60) likewise lying in the current circuit of the diaphragm adjustment motor (61).

5. X-ray examination apparatus according to claim 2, characterized in that there is connected in parallel with every one of the potentiometers (26, 27, 28) a signal lamp (29, 30, 31) characterizing the new photographic exposure position.

* * * * *